(12) United States Patent
Price et al.

(10) Patent No.: US 12,059,247 B2
(45) Date of Patent: Aug. 13, 2024

(54) APPARATUS FOR STATIC ASSESSMENT OF FOOT AND LOWER LIMB ABNORMALITIES

(71) Applicant: DYNASTAT SYSTEMS LTD, Penkridge (GB)

(72) Inventors: Mark Price, Penkridge (GB); Thomas Price, Penkridge (GB)

(73) Assignee: DYNASTAT SYSTEMS LTD, Penkridge (GB)

( * ) Notice: Subject to any disclaimer, the term of this patent is extended or adjusted under 35 U.S.C. 154(b) by 513 days.

(21) Appl. No.: 17/356,806

(22) Filed: Jun. 24, 2021

(65) Prior Publication Data
US 2021/0401323 A1 Dec. 30, 2021

(30) Foreign Application Priority Data
Jun. 26, 2020 (GB) .................................... 2009804

(51) Int. Cl.
*A61B 5/103* (2006.01)
*A61B 5/00* (2006.01)

(52) U.S. Cl.
CPC ............ *A61B 5/1036* (2013.01); *A61B 5/702* (2013.01); *A61B 2562/0247* (2013.01); *A61B 2562/046* (2013.01)

(58) Field of Classification Search
CPC .............................. A61B 5/1036; A61B 5/1074
USPC ........................................................ 33/515
See application file for complete search history.

(56) References Cited

U.S. PATENT DOCUMENTS

| | | | |
|---|---|---|---|
| 2,312,410 A * | 3/1943 | Hewitt, Jr. ............. | A43D 1/027 33/3 A |
| 4,062,355 A | 12/1977 | Kaye | |
| 4,802,494 A | 2/1989 | Gardiner | |
| 4,932,852 A * | 6/1990 | Suzuki ................. | A61B 5/1074 264/293 |
| 5,941,835 A * | 8/1999 | Sundman ............. | A61B 5/1036 600/592 |
| 5,979,067 A | 11/1999 | Waters | |
| 6,219,939 B1 | 4/2001 | Tasker et al. | |
| 6,782,630 B2 * | 8/2004 | Root ......................... | A61F 5/14 33/515 |
| 7,617,068 B2 * | 11/2009 | Tadin ................... | A61B 5/1036 356/600 |
| 7,685,728 B2 | 3/2010 | Goonetilleke et al. | |

(Continued)

FOREIGN PATENT DOCUMENTS

| | | |
|---|---|---|
| CN | 111449633 A | 7/2020 |
| EP | 1880702 A2 | 1/2008 |

(Continued)

OTHER PUBLICATIONS

UK Search Report for Application No. GB2009804.2 dated Apr. 6, 2021 (3 pages).

(Continued)

*Primary Examiner* — George B Bennett
(74) *Attorney, Agent, or Firm* — ALSTON & BIRD LLP

(57) ABSTRACT

An apparatus for static weight-bearing assessment of foot and lower limb abnormalities, the apparatus comprising: a platform configured to support at least part of a patient's foot; and an actuator arrangement configured to control a displacement of the platform.

18 Claims, 3 Drawing Sheets

(56) References Cited

U.S. PATENT DOCUMENTS

Figure 4:
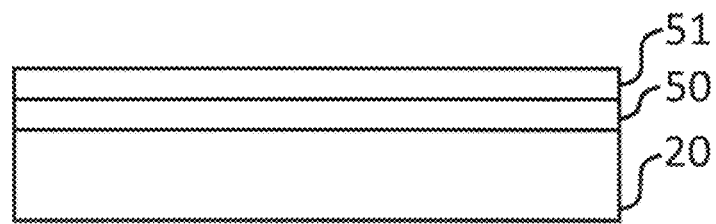

| | | | |
|---|---|---|---|
| 7,950,163 B2 * | 5/2011 | Lo | A61B 5/1036 33/515 |
| 8,290,739 B2 * | 10/2012 | Tadin | A61B 5/1036 600/595 |
| 9,867,555 B1 * | 1/2018 | Thomas | A61B 5/1072 |
| 11,733,508 B2 * | 8/2023 | Hsieh | A61B 5/1036 33/3 C |
| 2010/0106061 A1 * | 4/2010 | Lott | A43D 1/025 600/592 |
| 2015/0128354 A1 * | 5/2015 | Greenstein | A61B 5/1036 5/710 |
| 2015/0268037 A1 * | 9/2015 | Cook | G01B 11/2518 356/601 |
| 2016/0072986 A1 * | 3/2016 | Jones | H04N 23/51 348/77 |
| 2020/0275742 A1 * | 9/2020 | Kim | G06Q 30/06 |

FOREIGN PATENT DOCUMENTS

| | | |
|---|---|---|
| KR | 2019-0051643 A | 5/2019 |
| NL | 8701013 A | 11/1988 |
| WO | WO-2006/003640 A1 | 1/2006 |

OTHER PUBLICATIONS

Extended European Search Report for EP Application No. 21179256.9 dated Nov. 17, 2021 (26 pages).

* cited by examiner

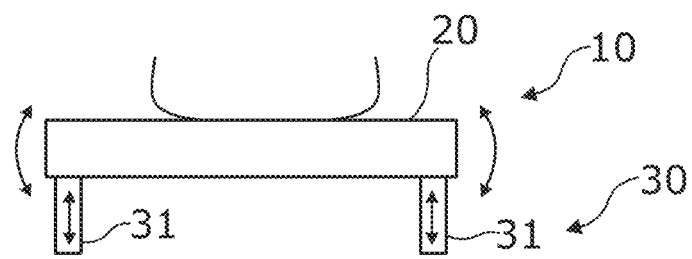
FIG. 1
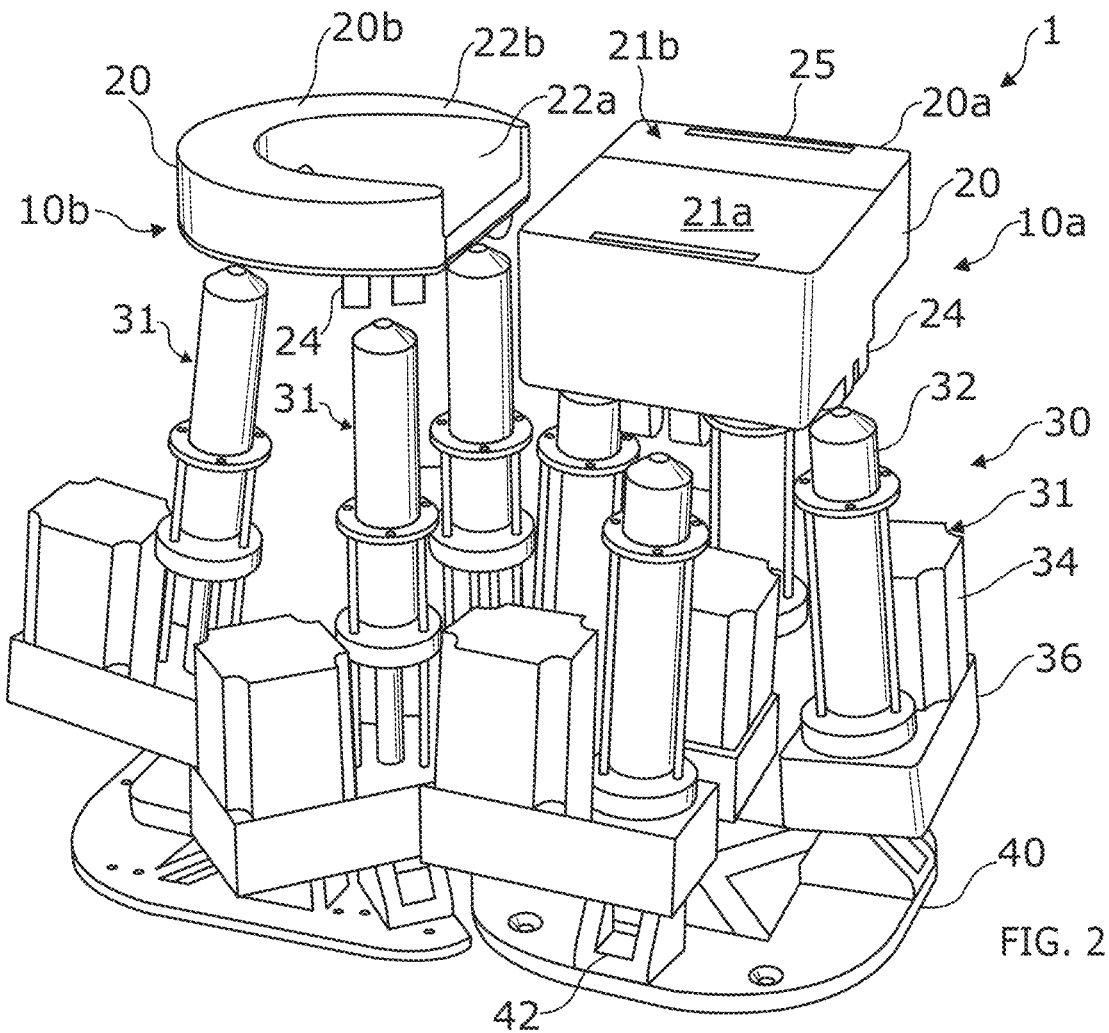
FIG. 2
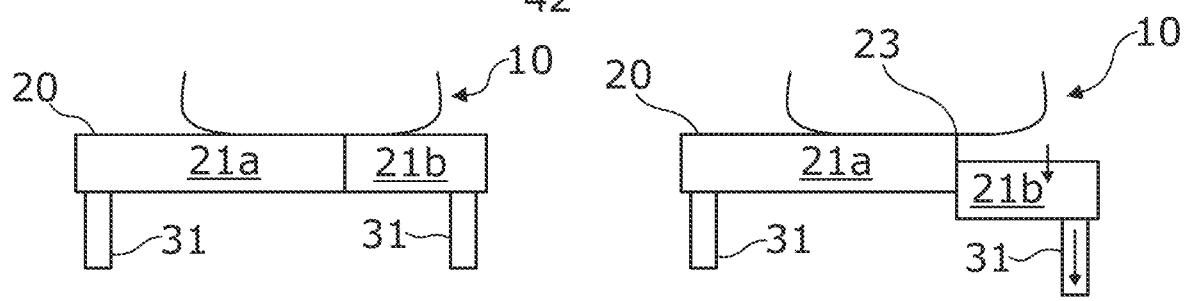
FIG. 3A
FIG. 3B

APPARATUS FOR STATIC ASSESSMENT OF FOOT AND LOWER LIMB ABNORMALITIES

CROSS-REFERENCE TO RELATED APPLICATIONS

This application claims priority to United Kingdom Patent Application No. 2009804.2, filed Jun. 26, 2020, the entire contents of which are incorporated herein by reference.

TECHNOLOGICAL FIELD

Embodiments of the present disclosure relate to an apparatus for static assessment of foot and lower limb abnormalities, and to a system.

BACKGROUND

A patient's foot posture can be analysed using static (closed-chain) tests. A static test may be performed on a tiltable platform on which the patient stands. An operator can determine a required correction of the foot posture, affecting a range of joints within the foot such as the subtalar, midtarsal and first ray joint.

An advantage of static testing is that the platform can be adjusted several times during a consultation, until the patient's foot is properly supported. However, known types of static testing apparatus are unergonomic for the operator, because the operator has to repeatedly kneel down and stand up in order to make adjustments and to take measurements by visual inspection. The patient may also have to step off the apparatus so that the operator can make adjustments.

BRIEF SUMMARY

According to various, but not necessarily all, embodiments there is provided an apparatus for static weight-bearing assessment of foot and lower limb abnormalities, the apparatus comprising:
 a platform configured to support at least part of a patient's foot; and
 an actuator arrangement configured to control a displacement (angular and/or linear) of the platform.

An advantage is a more ergonomic apparatus. The operator can change the static angular or linear position of the platform by using a human-machine interface to transmit control signals to the actuator arrangement. The patient may not need to step off the platform during this process.

In some examples, the apparatus comprises an input interface configured to receive control signals from an external human-machine interface, to control the actuator arrangement. This further improves ergonomics, because the operator can control the actuation of the platform remotely. The positions of the actuators may be monitored, to enable the operator to remotely measure the displacement of the platform.

In some examples, the apparatus comprises sensing means configured to measure information dependent on the patient's static foot posture, for a given position of the platform. An advantage is that the operator can quantitatively and directly verify the effect of displacing of the platform on the patient's static foot posture, in a weight-bearing condition.

In some examples, the apparatus comprises an output interface configured to output data indicative of the sensed information to an external computing device or external rendering device. This further improves ergonomics, because the operator can take static measurements remotely, without having to kneel down.

The movable static-testing platform, the actuator arrangement and the sensing means, if provided together, enable rapid diagnosis and verification, in a manner that is fast and ergonomic for the operator.

In some examples, the sensing means comprises a tactile sensor. A tactile sensor is a type of sensor that measures information arising from physical (touch) interaction with the environment. The tactile sensor measures information dependent on contact of the patient's foot on the platform. The information indicates which parts of the underside of the foot are touching the platform and which parts are not touching the platform. An advantage is improved diagnostic information, because abnormalities in the foot's contact area and pressure is a direct indicator of foot or lower limb abnormalities, such as incorrect pronation. The operator can measure peak pressures to inform their diagnosis. The operator can then displace the platform until the pressures are sufficiently distributed. When an optimal solution is found, an orthosis can be designed to replicate the measured displacement.

In some examples, the sensing means comprises a multi-dimensional array of sensels (sensor elements), for example to obtain a two-dimensional image of the contact surface. If a tactile sensor is used, the tactile sensor may comprise a multi-dimensional array of tactels, to obtain the two-dimensional image. A tactel is a tactile element, which is a type of sensel that is capable of detecting normal forces. An advantage is improved diagnostic information, because measuring abnormalities in a patient's weight distribution both along and across the foot, and between feet, can provide useful feedback to the operator for finding the optimal foot posture correction.

In some examples, the array of tactels is configured to produce an image when scanned, wherein the image indicates the information at a spatial resolution dependent on a spatial density of the tactels. The spatial density may be at least ten tactels per square inch for identifying small scale high-pressure regions. In an experiment, a spatial density of approximately 27 tactels per square inch produced a high-resolution image. If pressure-dependent information is sensed, the image may be a pressure map (or force map). In this implementation, the sensing means may be regarded as a pressure mapping sensor.

If a tactile sensor is used, the sensed information may be pressure-dependent information, responsive to variation of pressure and/or normal force across the contact surface. This is an indicator of a patient's weight distribution across the foot.

In some examples, the sensing means has a sensitivity sufficient to enable variation of the measurand across the contact surface to be measured. For example, the bit-depth of the sensed information may be at least four (16 levels), or optimally eight (256 levels). In the case of a tactile sensor, the image may be a pressure map with a plurality of pressure levels, to identify specific regions of the foot that are bearing too much or too little pressure.

As stated, the actuator arrangement is configured to displace the platform between static test displacements. In some examples, the displacements are different angles of the platform.

In some examples, the actuator arrangement is configured to tilt the platform in the sagittal plane, about a pitch axis, to replicate flexion. In some examples, the actuator arrangement is configured to tilt the platform in the frontal plane, about a roll axis, to replicate inversion and eversion. The actuator arrangement may be configured to permit three-dimensional tilting of the platform, about both pitch and roll rotation axes. The platform may be able to adopt a tilt angle that is displaced about both axes. The platform may be displaceable to move the origin of rotation. An advantage of the three-dimensional tilting capability is that the apparatus can better compensate for foot and lower limb abnormalities, because several joints in the ankle and foot are three-dimensional in their freedom of motion. Therefore, the apparatus has sufficient degrees of freedom to account for the often-underestimated complexity of gait and posture, and the role of the human foot.

In some examples, the actuator arrangement is configured to translate the platform. For example, the actuator arrangement may be configured to control a height of the platform. An advantage is that the apparatus can compensate for unequal leg length, when the apparatus is provided under each foot. In some examples, the actuator arrangement is configured to both tilt and translate the platform, for compensation of unequal leg length and foot posture.

In some examples, the actuator arrangement comprises at least three actuators, collectively arranged to provide at least three degrees of freedom of control, such as pitch, roll, and height.

In some examples, the actuator arrangement comprises linear actuators. Therefore, the output of the actuator moves linearly. Differential linear motion of different actuators controls tilt. Identical linear motion controls translation.

In some examples, the actuator arrangement comprises screw drive linear actuators. An advantage is superior torque, and superior holding force for conducting static tests. The actuator arrangement may be configured to dead-lift an adult human, so that the patient does not have to step off the apparatus when an adjustment is made.

In some examples, the actuator arrangement is stepper-controlled. Several advantages were identified to using stepper motors rather than other actuators. Stepper motors enable nonbinary positional control. Stepper motors provide fine positional control with high precision. Stepper motors provide high torque from static, so that a patient may not need to remove their weight during platform displacement. Stepper motors can actuate slowly but accurately, so as not to de-stabilise the patient. Stepper motors can be ramped to further reduce jerk.

In some examples, the actuators of the actuator arrangement are weight-bearing, transmitting the load of the patient to a base of the apparatus. In some examples, the actuator arrangement comprises actuators that are upstanding and splayed outwardly, so that the load is spread widely. An advantage is improved resistance to tipping, if the patient shifts their weight.

In some examples, the platform is shaped and sized to accommodate the forefoot of the patient. In some examples, the forefoot platform comprises a first platform portion and a second platform portion, wherein the first and second platform portions are movable out-of-plane relative to each other, to enable a first metatarsal region of the patient's foot to overhang a lateral edge of the first platform portion in the out-of-plane condition. An advantage is that the apparatus can better compensate for foot and lower limb abnormalities, because abnormalities caused by, or affecting the first metatarsal can be assessed.

In some examples, the actuator arrangement of the forefoot platform is configured to move the first and second platform portions relative to each other. An advantage is improved ergonomics, as the operator does not have to kneel down and adjust the platform portions.

In some examples, the actuator arrangement of the forefoot platform comprises at least three actuators coupled to the first platform portion, and at least one actuator coupled to the second platform portion. An advantage is that the platform portions can be moved out-of-plane while also being able to control other translations such as pitch, roll or height.

In some examples, a separate hindfoot apparatus may be provided, so that in use a single foot is supported by two apparatus spaced apart in the anterior direction. The forefoot and hindfoot apparatus may comprise their own actuator arrangements. Therefore, the forefoot platform and the hindfoot platform may be independently actuatable, each with the same or different numbers of degrees of freedom. An advantage of the independently actuatable platforms is that the apparatus can better compensate for foot and lower limb abnormalities, because the operator can take more accurate measurements of the neutral or relaxed position of the subtalar joint and mid tarsal joint when in a weight bearing position.

In some examples, the hindfoot platform comprises a guide surface shaped to position at least the hindfoot region of the patient's foot. The guide surface may be a recess. The guide surface may be a U-shaped recess to conform to the back of a heel. The guide surface enables the patient to place their foot accurately, to reduce variability between experiments.

According to various, but not necessarily all, embodiments there is provided a system comprising the forefoot apparatus and the hindfoot apparatus, for one foot to stand on.

Alternatively, the forefoot platform and the hindfoot platform may be merged into a single platform.

According to various, but not necessarily all, embodiments there is provided examples as claimed in the appended claims.

BRIEF DESCRIPTION

Figure 5:
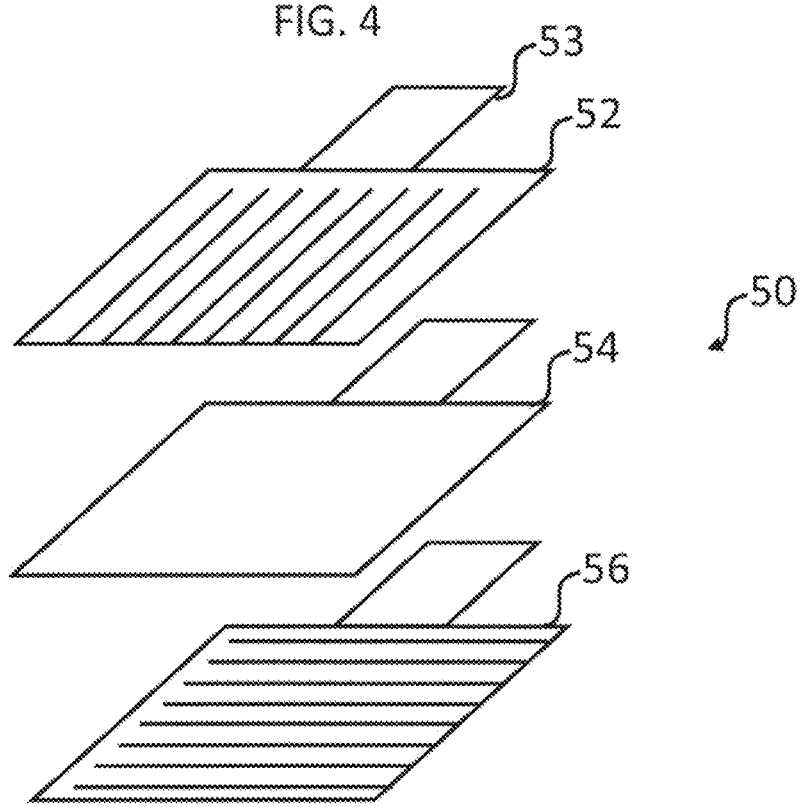
Figure 6:
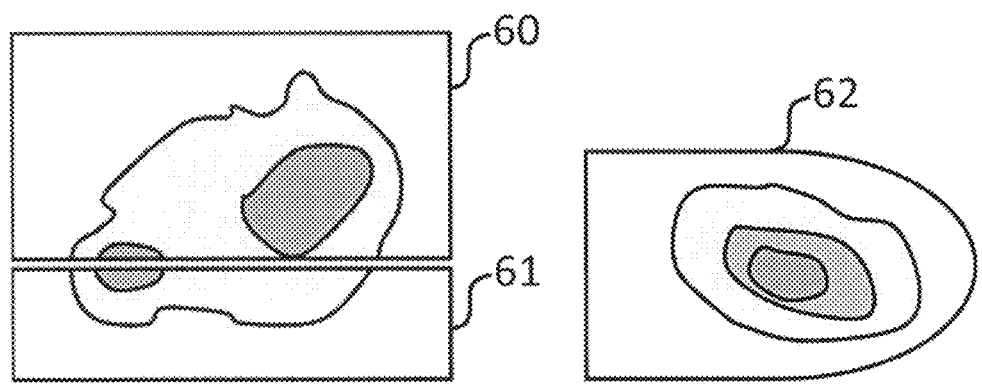
Figure 7:
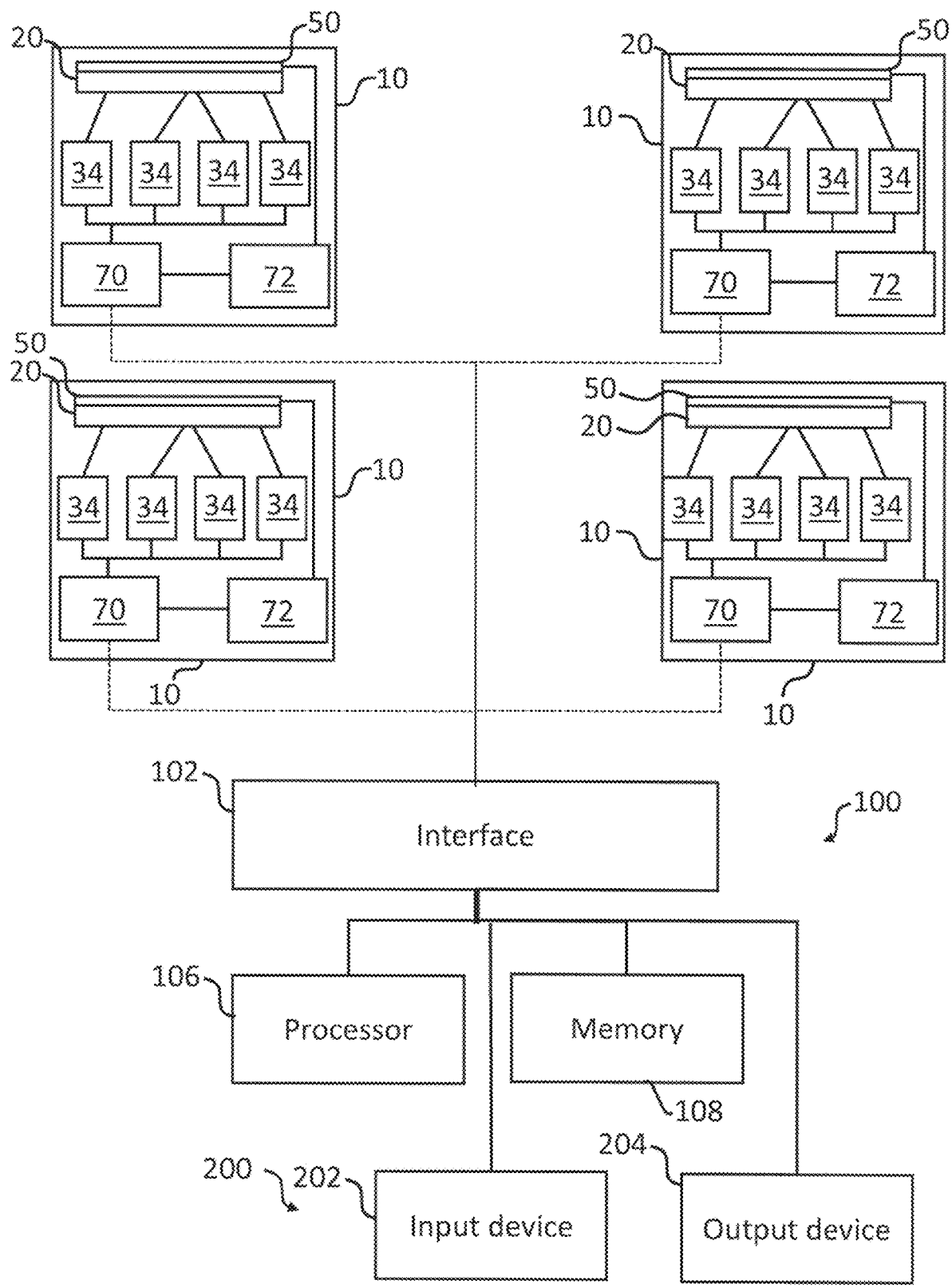

Some examples will now be described with reference to the accompanying drawings in which:

FIG. 1 schematically illustrates an example of an apparatus;

FIG. 2 schematically illustrates an example of a system comprising a forefoot apparatus and a hindfoot apparatus;

FIGS. 3A, 3B schematically illustrate an example of an apparatus in which portions of a same platform are movable out-of-plane relative to each other;

FIG. 4 schematically illustrates an example of an apparatus comprising sensing means;

FIG. 5 schematically illustrates an example of layers of a sensor array;

FIG. 6 schematically illustrates an example of images produced by a pressure mapping sensor; and FIG. 7 schematically illustrates an example of a system comprising the apparatus, a control system, and a human-machine interface.

DETAILED DESCRIPTION

FIG. 1 schematically illustrates an example of an apparatus 10 for static weight-bearing assessment of foot and lower limb abnormalities, the apparatus 10 comprising: a platform 20 configured to support at least part of a patient's foot; and an actuator arrangement 30 configured to control a displacement of the platform 20. FIGS. 2 and 3A, B are more detailed implementations of the platform 20 and actuator arrangement 30 of FIG. 1.

The platform 20 comprises a generally planar foot-bearing surface that is sufficiently wide in the lateral direction to accommodate the lateral width of one adult human foot. For example, the width of the platform 20 may be at least ten centimetres. The width of the platform 20 may be no greater than 30 centimetres. This does not need to be sufficiently wide to accommodate the lateral width of two adult human feet, because each foot stands on separate platforms. The anterior length of the platform 20 may be at least ten centimetres. The anterior length may be no greater than 20 centimetres, which is shorter than an adult human foot, so that only a portion of the foot is supported. This is because in later examples, the forefoot and hindfoot are supported by separate platforms. Alternatively, the whole foot may be supported by a single platform 20.

As shown in FIG. 1, the platform 20 is elevated above the ground by the actuator arrangement 30. However, it is not essential to every implementation that the actuator arrangement 30 is beneath the platform 20.

The actuator arrangement 30 comprises a plurality of actuators 31, of which two are visible in FIG. 1. As shown in other examples illustrated by the other Figures, more than two actuators could be provided if more degrees of freedom of tilt is desired.

In FIG. 1, but not necessarily in all examples, the actuators 31 are linear actuators. Differential extension or retraction of the left and right linear actuators 31 controls a tilt angle of the platform 20. Identical linear motion of the actuators 31 controls the height of the platform 20. The maximum range of articulation of the platform 20 may be at least ±5 degrees in the tilt axis or axes. In an implementation, the maximum range of articulation is approximately ±10 degrees in each tilt axis.

FIG. 2 illustrates a more detailed implementation of the apparatus 10 of FIG. 1, in which a system 1 of separate platforms 20a, 20b are provided for the forefoot and the hindfoot. The forefoot platform 20a is separated from the hindfoot platform 20b by a gap. FIG. 2 further illustrates optional details including: the shapes of the platforms 20a, 20b; platform hinges 24; the actuators 31; lower hinges 42; and a base 40. These optional features may be applied alone or in combination.

In FIG. 2, but not necessarily in all examples, the forefoot platform 20a and the hindfoot platform 20b are actuatable independently from one another. In FIG. 2, the forefoot platform 20a and the hindfoot platform 20b are actuatable independently from one another by different, non-overlapping sets of actuators 31, such that the forefoot platform 20a and the hindfoot platform 20b are separate apparatus 10. In an alternative implementation, the actuation of the platforms could be semi-independent, and/or the platforms could comprise a shared actuator 31. The independent actuation enables the forefoot section to be slightly offset to the linear bisection of the hindfoot. This is because the centre of the heel is laterally deviated to the centre line (bisection) of the forefoot.

In FIG. 2, the actuator arrangement 30 of the hindfoot platform 20b comprises three actuators 31. The three actuators 31 support the underside of the hindfoot platform 20b at different locations around the periphery of the hindfoot platform 20b, angularly separated by 120 degrees relative to each other. Differential extension or retraction of the three actuators 31 can tilt and roll the platform. Identical extension or retraction of the three actuators 31 can change the height of the platform.

In FIG. 2, the actuator arrangement 30 of the forefoot platform 20a comprises four actuators 31. The function of the fourth actuator 31 is described later.

In FIG. 2, but not necessarily all examples, the forefoot apparatus 10a is not fixed to the hindfoot apparatus 10b by a common base 40/structure, and can therefore be moved relative to the hindfoot apparatus 10b. This enables different foot lengths to be easily compensated for, by moving the forefoot apparatus 10a closer or further away in an anterior direction. However, in alternative implementations, the forefoot apparatus 10a and the hindfoot apparatus 10b may be fixed to each other on a same structure.

In FIG. 2, but not necessarily all examples, the actuators 31 are upstanding but splayed outwardly. The separation between the actuators 31 grows with decreasing height. This spreads the load and improves tip-resistance. In an example implementation, the angle of each actuator 31 may be no more than five degrees from vertical when the hind foot platform 20 is at its highest position and not tilted.

In FIG. 2, the hindfoot platform 20b comprises a U-shaped hindfoot guide surface 22a. The shape of the guide surface 22a is configured to enable the hindfoot of a patient's foot to be placed in a predetermined position on the hindfoot platform 20b, in a predetermined orientation.

In FIG. 2, the guide surface 22a is recessed relative to the surrounding raised platform surface 22b. The nominal lateral width of the recess is at least approximately eight centimetres, which is wide enough to receive a human hindfoot. The nominal maximum depth of the recess in the posterior direction is at least approximately six centimetres, which enables the hindfoot to be inserted sufficiently far, in the posterior direction, that the lateral sides of the recess can effectively restrict adduction or abduction of the foot.

Although the guide surface 22a in the illustrated example is a U-shaped recess, it would be appreciated that the guide surface 22a may be any shape that conforms generally to the curvature of a substantial portion of the hindfoot, controlling the position and orientation of the foot.

It would also be appreciated that a guide surface may conform to a different part of the foot than the hindfoot. For example, a forefoot guide surface may be provided on the forefoot platform 20a in addition to, or instead of, a hindfoot guide surface. However, an advantage of a hindfoot guide surface 22a is that it can be symmetrical about the anterior plane, while still accommodating left feet and right feet, because the hindfoot regions of the left foot and the right foot tend to be similarly shaped. By contrast, a forefoot is strongly asymmetrical due to the toes, so a forefoot guide surface 22a may need separate left-foot and right-foot platforms 20.

It would be appreciated that a guide surface is optional. A guide marking may be provided instead of a guide surface, or no guide may be provided at all.

The illustrated forefoot platform 20a will now be described. Unlike the hindfoot platform 20b, the forefoot platform 20a in the illustrated configuration comprises a planar surface across its whole surface area.

Optionally and as shown in FIGS. 2 and 3B, the forefoot platform 20a may comprise a movable portion 21b that can slide down, creating a stepped platform surface. The stepped platform surface exposes a lateral edge 23 of the first platform portion 21a, so that the first metatarsal of the foot overhangs the lateral edge 23. This enables conditions of the first metatarsal to be assessed. The lateral edge 23 is the left or right lateral edge of the first platform portion 21a closest to the second platform portion 21b.

The forefoot platform 20a can therefore be described as having a first platform portion 21a and a second platform portion 21b, wherein the first platform portion 21a and the second platform portion 21b are movable between a first, in-plane configuration and a second, out-of-plane configuration.

In the first configuration, the first platform portion 21a and the second platform portion 21b are approximately in-plane with each other, so that the weight of the forefoot is borne by both the first platform portion 21a and the second platform portion 21b. FIGS. 2 and 3A show the first platform portion 21a and the second platform portion 21b in the first configuration.

FIG. 3B shows the first platform portion 21a and the second platform portion 21b in the second configuration. An actuator 31 slides the second platform portion 21b down to the out-of-plane configuration. As a result, the foot remains in contact with the first platform portion 21a but is no longer in contact with the second platform portion. The first metatarsal region of the foot will overhang the lateral edge 23 of the first platform portion 21a.

Although the relative movement of the first platform portion 21a and the second platform portion 21b is actuator-controlled, it would be appreciated that the relative movement could alternatively be manually controlled—however, the operator would have to kneel down to perform the adjustment.

To facilitate actuation of the second platform portion, the actuator arrangement 30 of the forefoot apparatus 10a may comprise an additional actuator 31 that is coupled only to the second platform portion 21b. This can be seen in FIG. 2. In FIG. 2, the hindfoot platform 20b comprises three actuators 31 whereas the forefoot platform 20a comprises four actuators 31. The first, second and third actuators 31 of the forefoot platform 20a support the first platform portion 21a. The fourth actuator 31 supports the second platform portion 21b. Differential extension of the fourth actuator 31 relative to the first, second and third actuators 31 results in out-of-plane movement. In FIG. 3B, but not necessarily all examples, the movement is sliding in a direction that is substantially normal to the substantially planar surface of the first platform portion 21a.

In FIG. 3B, but not necessarily all examples, the vertical sliding is downwards sliding by the fourth actuator 31. However, in other implementations, the first, second and third actuators 31 may slide the first platform portion 21a upwards.

In some implementations, the actuators 31 of the forefoot platform 20a may be controllable so that the second platform portion 21b remains in the same orientation as the first platform portion 21a, regardless of whether the forefoot platform 20a is in the first, in-plane configuration or the second, out-of-plane configuration.

In some examples, the second platform portion 21b may be attached to the first platform portion 21a, but free to slide vertically. The attachment may be via any suitable sliding joint.

In FIG. 2, but not necessarily all examples, the second platform portion 21b has a smaller surface area than the first platform portion 21a. The second platform portion 21b only supports the width of the first metatarsal head, whereas the first platform portion 21a supports the second, third, fourth and fifth metatarsal heads.

The design of the linear actuators 31 of FIG. 2 will be described in more detail. Each linear actuator 31 shown comprises: an outer tube 32; a piston (not shown); a stepper motor 34; and a belt drive housing 36. The illustrated design is an advantageous example of various usable linear actuator designs.

The linear actuator 31 comprises an outer tube 32 inside which is a piston (not shown). The piston may be tubular. The piston may couple to the platform 20. In other implementations, the coupling between the piston and the platform 20 may be indirect.

A tip of the piston comprises a mounting point. The mounting point may couple to the platform 20 via a hinged connection, to enable tilting. In FIG. 2, the platform 20 comprises hinges 24 to receive the mounting points of the pistons. The hinges 24 are shown on the undersides of the platforms 20, but could be elsewhere in other implementations. Each mounting point (e.g. hinge 24) is positioned approximately halfway along a corresponding platform edge, representing a mid-point attachment.

For the illustrated platform 20a supported by four actuators 30, the four corresponding mounting points are located at different quadrants around the platform edge. The mounting points have 90-degree rotational symmetry around the platform 20a. The four mounting points enable both sagittal tilting and frontal tilting. For a platform 20b supported by three actuators 30, the three mounting points may have 120-degree rotational symmetry around the platform 20b. The three mounting points enable both sagittal tilting and frontal tilting.

If the actuator 31 is a screw-drive actuator, a screw mechanism such as a leadscrew (hidden from view) may extend or retract the piston.

In FIG. 2, but not necessarily in all examples, the stepper motor 34 is packaged alongside the outer tube 32, rather than at the end of the outer tube 32, to reduce the overall height of the platform 20 so that patients do not have to negotiate a high step. A further benefit is that weight is not transferred to ground via the stepper motor 34.

In order to transmit torque from the stepper motor 34 to the output (e.g. leadscrew), a torque path is provided. FIG. 2 illustrates a housing 36 within which is the torque path. The torque path may comprise a belt drive. Alternatively, the torque path may comprise a chain drive or gears.

The illustrated belt drive housing 36 is configured to be weight-bearing. Each actuator 31 may be configured to support up to 75 kilograms or more. The housing 36 may be composed of a sufficiently thick metal, for example. In some implementations, each actuator 31 may be configured to support up to 185 kilograms or more.

The lower mounting point of the actuator 31 is, in this example, provided on the underside of the belt drive housing 36. The lower mounting point couples to a base 40 of the apparatus 10 via a hinged connection. In FIG. 2, the base 40 is a plate. An upper side of the plate comprises hinges 42, wherein each hinge 42 receives a lower mounting point of an actuator 31.

In the illustrated example, the weight of the patient is distributed across the platform 20, then to the pistons, then to the outer tubes 32, then to the belt drive housings 36, and then to lower mounting points where the actuators 31 mount to a base 40 of the apparatus 10.

FIG. 4 illustrates an example of sensing means 50 provided on the platform 20, between the platform surface and the patient's foot. In some, but not necessarily all examples, the sensing means 50 is a tactile sensor. The tactile sensor measures pressure-dependent information, responsive to variation of pressure and/or force across the contact surface between the underside of the foot and the platform 20.

The tactile sensor 50 is illustrated as a layer in FIG. 4. According to an example implementation, the tactile sensor may be a pressure mapping sensor 50, comprising a two-dimensional array of tactels. The average spatial density of the tactels may be at least 10 per square inch, or approximately 20-30 per square inch in an implementation.

The pressure mapping sensor 50 may be adhered to the platform 20 by a suitable adhesive. The pressure mapping sensor 50 may be covered by a thin protective layer 51 such as a polyurethane sheet, separating the pressure mapping sensor 50 from direct skin contact. The protective layer 51 can be cleaned between uses.

FIG. 5 illustrates an example implementation of the pressure mapping sensor 50. The pressure mapping sensor 50 comprises an array of force-sensing resistors. The array of force-sensing resistors is created by at least three layers 52, 54, 56, which are adhered to each other, for example via spacer layers. The first layer 52 comprises columns of conductive traces. The third layer 56 comprises rows of conductive traces. A tactel is defined as the intersection between a row trace and a column trace. The second layer 54 is between the first layer 52 and the third layer 56, separating them from each other. The second layer 54 comprises force-sensitive material. An example of force-sensitive material is a film comprising a mix of electrically conducting and non-conducting micro-particles or nano-particles suspended in a matrix.

In an example implementation, the second layer 54 is one of a plurality of intermediate layers. The intermediate layers comprise one or more force-sensitive resistor layers and one or more dielectric layers therebetween. The force-sensitive resistor layers are configured to change their resistance in dependence on applied force. The force-sensitive resistor layers comprise a plurality of force-sensitive resistors on a substrate. For example, the force-sensitive resistors may be printed on the substrate. The dielectric layers include a dielectric dot layer. The dielectric dot layer comprises a plurality of dielectric dots, each dot corresponding to a tactel.

As normal pressure is applied, the resistance of the force-sensitive material changes. By measuring the potential difference or electric current of each tactel at the changed resistance, the resistance change can be converted to a pressure value.

The nominal electrical resistance and voltage of the pressure mapping sensor 50 may be selected to ensure its maximum electrical current is below a pain threshold (no greater than approximately 2 mA), or optimally below a sensation threshold (no greater than approximately 1 mA).

It would be appreciated that instead of force-sensing resistors, other force-sensing elements such as force-sensing capacitors could be used.

For the system 1 shown in FIG. 2, separate pressure mapping sensors 50 may be provided on the first platform portion 21a, the second platform portion 21b, and the hindfoot guide surface 22a. Therefore, the total sensing area for a whole foot is discontinuous. The discontinuities between the sensors accommodate unrestricted relative movement of the platforms. The pressure mapping sensors 50 may be provided on separate substrates, rather than a common substrate.

The first and third layers 52, 56 of the pressure mapping sensor 50 may electrically connect with controlling circuitry via any suitable interconnect cable, such as a flexible flat cable 53 (FFC) as shown in FIG. 5. In some examples, the FFC 53 is a continuation of one or more of the layers 52, 54, 56. The FFC 53 may extend part, or all the way to the relevant circuitry.

The platforms 20 may comprise suitable conduits adjacent to the pressure mapping sensors 50, to enable the interconnecting cables of the pressure mapping sensors 50 to be routed downwards through the platforms 20, without protruding from the sides of the platforms where they may get caught by the patient's foot. If FFCs 53 are used as the interconnect cables, the conduits may be thin slots 25 as shown in FIG. 2. FIG. 2 shows a slot 25 in the second platform portion 20b that is parallel to, and adjacent to a lateral edge of the forefoot platform 20a. The slots 25 are between the pressure mapping sensors 50 and the lateral edges.

The pressure mapping sensor 50 produces an image when scanned. An example of a pressure map image is shown in FIG. 6. FIG. 6 shows three images 60, 61, 62, comprising a first image 60 from a pressure mapping sensor 50 on the first platform portion 21a of the forefoot platform 20a, a second image 61 from a pressure mapping sensor 50 on the second platform portion 21b of the forefoot platform 20a, and a third image 62 from a pressure mapping sensor 50 on the hindfoot platform 20b. Darker contoured regions in the images represent regions of greater relative pressure. The pressure maps may be spatially interpolated by a processor to form the image.

The above-described design of FIG. 5 has a high sensitivity. The sensitivity may be configurable. For example, the force sensitivity may be configurable to between approximately 0.1 kg and approximately 6 kg. A bit depth of eight (256 values) can accurately discriminate between different levels of pressure.

As shown in FIG. 7, the apparatus 10 may be controlled remotely, without the operator having to kneel down. For example, the actuator arrangement 30 can be controlled remotely and/or the sensors can be read remotely.

Each apparatus 10 of FIG. 7 comprises an input interface 70, to enable control of the actuator arrangement 30. The input interface 70 is configured to receive control signals from an external human-machine interface. If the actuators 31 comprise stepper motors 34, the input interface 70 is operably coupled to the stepper motors 34, so that the control signals can control the stepper motors 34. In an example implementation, the control signals may be open-loop control signals, depending on the type of actuator 31. The input interface 70 may be a wired interface or a wireless interface. In an example implementation, a Serial Peripheral Interface (SPI) bus is used to transmit control signals from the input interface 70 to the actuators 31.

FIG. 7 further illustrates an external control system 100 configured to transmit the control signals. The external control system 100 comprises at least one processor 106 and at least one memory 108. The memory 108 is electrically coupled to the processor 106. The memory 108 has computer program code stored therein. The memory 108 and the computer program code are configured to, with the at least one processor 106:

receive an instruction from a human-machine interface 200, indicating a desired displacement of the platform 20;

convert the instruction to control signals for controlling the plurality of actuators 31; and transmit the control signals to the input interface 70 of the apparatus 10, the input interface 70 being coupled to the actuators 31.

The control signals may be pulse signals, for example. The processor 106 may ramp the pulse signals when accelerating or decelerating the stepper motor 34, to reduce jerk.

The external control system 100 comprises an input/output interface 102, for transmitting the control signals to the input interface(s) 70 of the apparatus 10. If the input/output interface 102 is provided on a separate control board from the processor 106 and memory 108, the input/output interface 102 may be coupled to the processor 106 and memory 108 via an appropriate communication standard.

Each apparatus 10 of FIG. 7 further comprises sensor circuitry 72 configured to scan the sensing means 50, and an output interface, configured to output data indicative of the information sensed by the sensing means, to the external computing device or to an external rendering device. In FIG. 7, but not necessarily all examples, the output interface and the input interface are part of a same input/output interface 70. In FIG. 7, but not necessarily all examples, the data is transmitted to the external control system 100.

Each apparatus 10 may comprise a sensor board configured to apply voltage to the sensing means, configured to scan the sensing means, and configured to provide the output interface. The output interface may be a wired or wireless output interface.

The input/output interface 104 is also configured to receive the data from the output interface(s) of the apparatus 10. The input/output interface may comprise an analog-to-digital converter, or the data may have already been converted at the apparatus 10.

In some, but not necessarily all examples, the control system 100 further comprises a wired or wireless network interface (not shown) to enable client devices to operably couple to the control system 100 over a short range communication network or long range communication network. The network interface may comprise an Ethernet port, a Universal Serial Bus port, a wireless transceiver, and/or the like.

FIG. 7 further illustrates an external human-machine interface 200. The human-machine interface 200 is operably coupled to the control system 100, either by integration into a common device comprising the control system 100, or as part of a separate device connected via the network interface. The human-machine interface 200 comprises an input device 202, such as a keyboard and/or mouse, enabling operator control of the actuators 31. The human-machine interface 200 comprises an output/rendering device 204, such as a display, enabling visualization of processed data from the sensing means, such as the image of FIG. 6.

The processor 106 may be configured to perform image processing on the data from the sensing means, and to cause visualization of the processed data on the output device 204. An example of image processing includes spatial interpolation of pressure/force data between individual tactels, to smooth the image. Another example of image processing includes temporal integration of the data scanned at different times, to get rhomboid and other complex measures of overall stability and performance. Further, the pressure or force may be converted to normalized values, based on the patient's predetermined weight.

The angle/position of the apparatus 10 may be displayed concurrently to the images. The angle/position may be determined based on calibration data if the actuators 31 are open loop, or based on sensor measurements if the actuators 31 are closed loop. In an open loop implementation of a stepper motor 34, homing sensing is performed via EMF (electromotive force) feedback. The stepper motors 34 have sufficient cogging torque as to not skip steps under the designed load, not requiring feedback under operation.

Where a structural feature has been described, it may be replaced by means for performing one or more of the functions of the structural feature whether that function or those functions are explicitly or implicitly described.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this description, reference has been made to various examples. The description of features or functions in relation to an example indicates that those features or functions are present in that example. The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although examples have been described in the preceding paragraphs with reference to various examples, it should be appreciated that modifications to the examples given can be made without departing from the scope of the claims.

Features described in the preceding description may be used in combinations other than the combinations explicitly described above.

Although functions have been described with reference to certain features, those functions may be performable by other features whether described or not.

Although features have been described with reference to certain examples, those features may also be present in other examples whether described or not.

The term 'a' or 'the' is used in this document with an inclusive not an exclusive meaning. That is any reference to X comprising a/the Y indicates that X may comprise only one Y or may comprise more than one Y unless the context clearly indicates the contrary. If it is intended to use 'a' or 'the' with an exclusive meaning then it will be made clear in the context. In some circumstances the use of 'at least one' or 'one or more' may be used to emphasis an inclusive meaning but the absence of these terms should not be taken to infer any exclusive meaning.

The presence of a feature (or combination of features) in a claim is a reference to that feature or (combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in some examples exactly as described and is present in other examples substantially as described.

Whilst endeavoring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:

1. An apparatus for static weight-bearing assessment of foot and lower limb abnormalities, the apparatus comprising:
    a platform configured to support at least part of a patient's foot; and
    an actuator arrangement configured to control a displacement of the platform,
    wherein the platform comprises a first platform portion and a second platform portion, wherein the first and second platform portions are movable out-of-plane relative to each other, to enable a first metatarsal region of the patient's foot to overhang a lateral edge of the first platform portion in the out-of-plane position, wherein the actuator arrangement is configured to move the first and second platform portions between a first configuration and a second configuration, wherein in the first configuration the first and second platform portions are in-plane with each other so that a weight of a forefoot of the patient's foot is borne by both the first and second platform portions, and wherein in the second configuration the second platform portion is out-of-plane relative to the first platform portion so that the patient's foot is in contact with the first platform portion but is no longer in contact with the second platform portion.

2. The apparatus of claim 1, comprising an input interface configured to receive control signals from an external human-machine interface, to control the actuator arrangement.

3. The apparatus of claim 1, comprising a tactile sensor configured to measure information dependent on a contact surface between the patient's foot and the platform.

4. The apparatus of claim 3, wherein the information is pressure-dependent information, responsive to variation of pressure and/or force across the contact surface.

5. The apparatus of claim 3, wherein the tactile sensor comprises:
    a multi-dimensional array of tactels, configured to produce an image when scanned, wherein the image indicates the information at a spatial resolution dependent on a spatial density of the tactels.

6. The apparatus of claim 5, wherein the tactile sensor is configured to output the image with a bit depth of at least four, and/or wherein the spatial resolution is at least ten tactels per square inch.

7. The apparatus of claim 3, comprising an output interface configured to output data indicative of the information to an external computing device or external rendering device.

8. The apparatus of claim 1, wherein the actuator arrangement is configured to control a height of the platform.

9. The apparatus of claim 1, wherein the actuator arrangement is configured to control an angle of the platform.

10. The apparatus of claim 9, wherein the actuator arrangement is configured to control the angle of the platform about multiple rotation axes.

11. The apparatus of claim 1, wherein the actuator arrangement comprises at least three actuators arranged to provide at least three degrees of freedom of control of the displacement of the platform.

12. The apparatus of claim 11, wherein the degrees of freedom comprise pitch, roll and height.

13. The apparatus of claim 1, wherein the actuator arrangement comprises linear actuators.

14. The apparatus of claim 13, wherein the linear actuators comprise screw drive linear actuators.

15. The apparatus of claim 1, wherein the actuator arrangement comprises actuators that are upstanding and splayed outwardly.

16. The apparatus of claim 1, wherein the actuator arrangement comprises at least three actuators coupled to the first platform portion, and at least one actuator coupled to the second platform portion.

17. The apparatus of claim 1, wherein the platform comprises a guide surface shaped to position at least a hindfoot region of the patient's foot.

18. A system for static weight-bearing assessment of foot and lower limb abnormalities, the system comprising a forefoot apparatus for a forefoot of a foot, and a hindfoot apparatus for a hindfoot of the foot, wherein the forefoot apparatus is an apparatus as claimed in claim 1, and wherein the hindfoot apparatus comprises: a platform configured to support the hindfoot, and an actuator arrangement configured to control a displacement of the platform of the hindfoot apparatus.

* * * * *